United States Patent [19]

Bartek et al.

[11] 4,255,283

[45] Mar. 10, 1981

[54] OXYDEHYDROGENATION PROCESS FOR ALKYLAROMATICS AND CATALYST THEREFOR

[75] Inventors: Joseph P. Bartek, University Heights; Robert K. Grasselli, Chagrin Falls, both of Ohio

[73] Assignee: The Standard Oil Company, Cleveland, Ohio

[21] Appl. No.: 889,177

[22] Filed: Mar. 23, 1978

Related U.S. Application Data

[62] Division of Ser. No. 792,637, May 2, 1977, abandoned.

[51] Int. Cl.³ .................... B01J 21/02; B01J 27/14
[52] U.S. Cl. ................................... 252/437; 252/432
[58] Field of Search ............................. 252/437, 432

[56] References Cited

U.S. PATENT DOCUMENTS

| | | | |
|---|---|---|---|
| 3,156,705 | 11/1964 | Kerr | 252/437 X |
| 3,346,617 | 10/1967 | Hiroki et al. | 252/437 X |
| 3,454,630 | 7/1969 | Yamaguchi et al. | 252/437 X |
| 3,642,930 | 2/1972 | Grasselli et al. | 252/437 X |
| 3,736,354 | 5/1973 | Yonogita et al. | 252/437 X |
| 3,761,424 | 9/1973 | Koferstein | 252/437 |
| 3,865,873 | 2/1975 | Oda et al. | 252/437 X |
| 3,873,633 | 3/1975 | Cichowski | 260/680 E |
| 3,925,464 | 12/1975 | Oda et al. | 252/437 X |
| 3,926,845 | 12/1975 | Cichowski | 252/432 |
| 3,933,932 | 1/1976 | Vrieland et al. | 260/669 R |
| 3,935,126 | 1/1976 | Vrieland et al. | 260/290 V |
| 3,951,861 | 4/1976 | Shinaishi et al. | 252/437 |
| 3,956,182 | 5/1976 | Ishimi | 252/437 X |
| 3,957,897 | 5/1976 | Vrieland et al. | 260/669 R |
| 3,980,585 | 9/1976 | Kerr et al. | 252/437 |
| 4,042,625 | 8/1977 | Matsuzawa et al. | 252/437 X |
| 4,051,179 | 9/1977 | Sonobe et al. | 252/437 X |
| 4,056,487 | 11/1977 | Kerr | 252/437 X |
| 4,072,708 | 2/1978 | White et al. | 252/437 X |

FOREIGN PATENT DOCUMENTS

| | | | |
|---|---|---|---|
| 2441109 | 6/1975 | Fed. Rep. of Germany | 252/437 |
| 42-16602 | of 1967 | Japan | 252/437 |

*Primary Examiner*—Delbert E. Gantz
*Assistant Examiner*—William G. Wright
*Attorney, Agent, or Firm*—Gary R. Plotecher; Herbert D. Knudsen; Larry W. Evans

[57] ABSTRACT

This invention relates to an improved process for the dehydrogenation of alkyl-substituted aromatic compounds to the corresponding alkenyl-substituted aromatics in the presence of oxygen and in the presence of an improved metal phosphate catalyst composition.

14 Claims, No Drawings

OXYDEHYDROGENATION PROCESS FOR ALKYLAROMATICS AND CATALYST THEREFOR

This is a division of application Ser No. 792,637, filed May 2, 1977.

BACKGROUND OF THE INVENTION

Current commercial dehydrogenation practices as for example in the conversion of ethyl benzene to styrene, suffer from the disadvantages of low conversions, while higher conversion oxydehydrogenations suffer from poor selectivities. Selectivity is especially important in this particular reaction since the starting materials for producing styrene comprise over 80 percent of its manufacturing costs. Thus there is a continuing search for catalytic materials that are more efficient in minimizing side reactions and improving conversion rates.

A number of catalysts and catalytic systems have been disclosed utilizing various phosphates and pyrophosphates for the conversion of alkyl aromatics to derivatives having side-chain unsaturation. For example U.S. Pat. No. 3,923,916 claims nickel pyrophosphate as a superior catalyst for the oxydehydrogenation of alkyl aromatics. U.S. Pat. No. 3,933,932 and U.S. Pat. No. 3,957,897 disclose the use of lanthanum, rare earth and alkaline earth phosphates, respectively, as oxydehydrogenation catalysts for alkyl aromatics. However catalyst compositions containing arsenic, antimony, bismuth or cadmium phosphates which have demonstrated outstanding activity for the dehydrogenation reaction of the present invention have heretofore not been disclosed. Although U.S. Pat. No. 3,873,633 utilizes a cobalt-bismuth-phosphorus-oxygen composition as a catalyst for the oxydehydrogenation of paraffinic hydrocarbons to monoolefins or diolefins, the use of this type of catalyst for the conversion of alkyl aromatics to unsaturated side-chain derivatives has heretofore not been known.

SUMMARY OF THE INVENTION

The present invention comprises the process for the oxydehydrogenation of alkyl-substituted aromatic compounds to the corresponding alkenyl-substituted aromatics and the novel catalyst compositions therefor. More specifically the invention comprises the oxydehydrogenation of alkyl aromatic compounds to form the corresponding unsaturated side-chain derivative wherein the alkyl aromatic contains at least one alkyl group having from two to six carbon atoms, and wherein the alkyl group is attached to only one aromatic ring. The aromatic may be a mononuclear or a condensed-ring dinuclear aromatic, or a corresponding nitrogen-containing heterocyclic aromatic.

The process comprises passing a gaseous mixture of molecular oxygen such as air and the alkyl aromatic compound in the presence or absence of a diluent such as steam, carbon dioxide, nitrogen, or an inert hydrocarbon, over a catalyst at a temperature of from about 300° to about 650° C., said catalyst having a composition represented by the empirical formula:

wherein
A is an alkali metal and or thallium;
M is one or more of the elements of nickel, cobalt, copper, manganese, magnesium, zinc, calcium, niobium tantalum, strontium or barium;
$M^1$ is one or more of the elements of iron, chromium, uranium, thorium, vanadium, titanium, lanthanum or the other rare earths;
$M^{11}$ is one or more of the elements of tin, boron, lead, germanium, aluminum, tungsten or molybdenum;
B is bismuth, tellurium, arsenic, antimony, cadmium, or combinations thereof;
P is phosphorus; and
wherein a through y have the following values:
a=0 to 20;
b=0 to 20;
c=0 to 20;
d=0 to 4;
e=0.1 to 20;
y=8 to 16;
x=the number of oxygens required to satisfy the valence requirements of the other elements present; and wherein the sum of b+c+e is greater than 1.

Preferred in this invention are catalyst compositions wherein
a=0 to 2;
b=4 to 12;
c=0.2 to 4;
d=0 to 2;
e=0.5 to 5; and
y10 to 14.

Contemplated within the scope of the present invention are the catalyst compositions represented by the empirical formula:

wherein A, M, $M^1$, $M^{11}$ B & P have the same compositions as has been hereinbefore designated, and wherein a through y have the following values;
a=0 to 5;
b=4 to 20;
c=0.1 to 10;
d=0 to 4;
e=0.1 to 12;
y=8 to 16;
x=the number of oxygens required to satisfy the valence requirements of the other elements present; and wherein the sum of 2b+3(c+e) is greater than 9 and less than 3y.

Preferred is the composition wherein:
a is in the range of 0–1;
b is in the range of 4 to 12;
c is in the range of 0.1 to 4;
d is in the range of 0 to 2;
e is in the range of 0.1 to 4; and the sum of 2b+3(c+e) is greater than 9 and less than 3y.

The catalysts of this invention are unexpectedly good oxydehydrogenation catalysts. For example in the dehydrogenation of ethyl-benzene to styrene, per pass conversions to styrene in the range of 70% and selectivities of up to 90% are obtained.

The catalysts useful in the instant process may be used alone or supported on a carrier. Suitable carrier materials include silica, Alundum, titania and mullite and particularly phosphate-type carriers such as zirconium phosphate, antimony phosphate, aluminum phosphate and especially boron phosphate. In general, the support may be employed in amounts less than 95% by weight of the final catalyst composition, and the catalyst may be incorporated in the carrier by coating, impregnation and coprecipitation.

These catalysts may be prepared by coprecipitation or by other methods known in the art. Generally they are prepared by mixing an aqueous solution of the metal nitrates with an aqueous solution of ammonium dihydrogen phosphate and drying this precipitate.

The catalyst may be calcined to produce desirable physical properties such as attrition resistance, optimum surface area and particle size. It is generally preferred that the calcined catalyst be further heat-treated in the presence of oxygen at a temperature of above 250° C. but below a temperature deleterious to the catalyst.

Among the alkyl aromatics contemplated to be within the scope of the invention are the mono-substituted aromatics such as, for example, ethyl benzene, isopropyl benzene, secondary-butyl benzene; disubstituted aromatics such as ethyl toluene, diethyl benzene, t-butyl ethyl benzene; trisubstituted aromatics such as the ethyl xylenes; condensed ring aromatics such as ethyl naphthalene, methyl ethyl naphthalene, diethyl naphthalene; and nitrogen-containing heterocyclic aromatics such as ethyl pyridine, methyl ethyl pyridine, ethyl quinoline, ethyl isoquinoline, and the like. Particularly preferred reactants in this reaction are ethyl benzene which is readily converted to styrene, diethyl benzene which is converted to mixtures of ethyl styrene and divinyl benzene, ethyl pyridine and methyl ethyl pyridine which are converted to vinyl pyridine and methyl vinyl pyridine, respectively.

The reaction may be conducted in a fixed-bed or a fluidized-bed reactor at temperatures as low as 300° C., although optimum temperatures for the dehydrogenation of the alkyl side-chains are in the range of from about 400° to 600° C., and there is no apparent advantage in operating at temperatures much in excess of 650° C.

The pressure at which the instant process is usually conducted is about atmospheric, although pressure of from slightly below atmospheric up to and above 3 atmospheres are operable.

The apparent contact time employed in the instant process may be within the range of 0.1 to 50 seconds, and for good selectivity and yields a contact time of from 1 to 15 seconds is preferred.

The molar ratio of oxygen to alkyl aromatic compound fed to the reactor can range from about 0.5 to about 4 moles of oxygen per mole of alkyl aromatic compound, but a preferred range is from about 0.5 to about 1.5 moles of oxygen per mole of aromatic compound. The oxygen employed may be in the form of pure oxygen, although the use of air is preferred for purposes of convenience.

Diluents such as steam, carbon dioxide, nitrogen, inert hydrocarbons or other inert gases may also be used and amount of from 0 to 20 volumes of diluent per volume of alkyl aromatic compound are suitable.

The following examples serve to illustrate the feasibility and the improvement obtained in the oxydehydrogenation process utilizing catalysts of the present invention as compared with catalysts of the prior art.

SPECIFIC EMBODIMENTS

Examples 1-26 are representative of the present invention and Comparative Examples A-E are representative of prior art processes.

CATALYST PREPARATIONS

Comparative Example A $Ni_2P_2O_7$

Nickel nitrate hexahydrate (168.5 g) was dissolved in 500 cc of water, and acidity was adjusted to a pH of 6.4 with ammonia. Ammonium dihydrogen phosphate (77.7 g) was dissolved in 250 cc of water, and the pH adjusted to 6.8 with ammonia. The solutions were mixed and stirred at room temperature for 15 minutes, after adjusting the pH to 6.0 with ammonia, then filtered. The light green precipitate was filtered, dried at 110° C. and heat-treated for 3 hours at 290° C., 3 hours at 427° C., and 2 hours at 550° C. to give a tan solid having a surface area of 14 $m^2/g$.

Comparative Example B-$Mg_2P_2O_7$

Magnesium nitrate hexahydrate (309.2 g) was dissolved in 60 cc of water with heating. Ammonium dihydrogen phosphate (138.2 g) was dissolved in 100 cc of water with heating. The solutions were mixed and stirred with heating until a white thick paste formed. The paste was dried at 110° C., heat-treated at 290° C. for 3 hours, 427° C. for 3 hours, and 550° C. for 16 hours in air to give a white solid having a surface area of 21.8 $m^2/g$.

Comparative Example C-$La_4 (P_2O_7)_3$

Lanthanum nitrate hexahydrate (Trona code 548) (130 g) was dissolved in 31.5 cc nitric acid and diluted to 250 cc with water. Ammonium dihydrogen phosphate (57.1 g) was dissolved in 250 cc of water and acidified to a pH of $\sim 1$ with 25 cc nitric acid. On mixing the solutions with stirring, an opalescence formed. After stirring 22 hours with heating a milky white precipitate formed. On heating to boiling, the gel thickened. The gel was filtered, dried at 110° C., heat-treated at 290° C. (3 hours), 427° C. (3 hours) and 550° C. (16 hours) in air to give a white solid having a surface area of 17 $m^2/g$.

Comparative Example D-$Co_7Fe_3P_{12}O_{41.5}$

Ferric nitrate nonahydrate (121.2 g) and cobalt nitrate hexahydrate (203.8 g) were dissolved in 10 ml. of water with heating. Ammonium dihydrogen phosphate (138.0 g) was dissolved in 100 ml of water with heating. The solutions were mixed and stirred with heating until a thick paste formed. The paste was dried at 110° C., then heat-treated at 290° C. (3 hours), 427° C. (3 hours) and 550° C. (3 hours) in air to give a blue solid with a surface area of 0.8 $m^2/g$.

Comparative Example E-$Co_2P_2O_7$

Cobalt nitrate hexahydrate (349.1 g) was dissolved in 20 cc of water with heating. Ammonium dihydrogen phosphate (138.0 g) was dissolved in 100 cc of water with heating. The solutions were mixed and stirred with heating until a thick purple paste formed. The paste was dried at 110° C., and heat-treated at 290° C. (3 hours), 427° C. (3 hours) and 550° C. (16 hours) to give a blue solid with a surface area of 12.2 $m^2/g$.

EXAMPLE 1

$Bi_8P_{12}O_{42}$

Bismuth nitrate pentahydrate (194 g), 5 cc nitric acid (conc.) and 45 cc of water were warmed to 75° C. with stirring. Ammonium dihydrogen phosphate (69.0 g) was added to 50 cc of water and warmed to 75° C. The two solutions were mixed, then stirred and heated until a white paste formed. The paste was dried at 110° C., heat-treated at 290° C. (5 hours), 427° C. (3 hours), and 550° C. (3 hours) in air. A white solid resulted with a surface area of 0.3 m²g.

EXAMPLE 2

25% $Bi_8P_{12}O_{42}$-75%$BPO_4$

Bismuth nitrate pentahydrate (19.4 g) was dissolved in 1 cc of nitric acid (conc.) and 9 cc of water, with heating. Ammonium dihydrogen phosphate (6.9 g) was dissolved in 25 cc of water. The solutions were combined, and 40.4 g boron phosphate were added. The boron phosphate powder (−200 mesh) was made by mixing 121 g of 85% $H_3PO_4$ with 62 g $H_3BO_3$, warming to 40° C. for 5 hours, drying the resulting paste at 110° C. and calcining in air at 300° C. (8 hours). After the $BPO_4$-addition the paste was dried at 110° C. and heat-treated as in Example 1. A white solid having a surface area of 17 m²/g resulted.

EXAMPLE 3

5%-$Cu_{1.5}BiP_5O_{15.5}$-95% $BPO_4$

A Boron phosphate powder was made from 45 g $H_3BO_3$ and 50 cc 85% $H_3PO_4$ by refluxing $H_3BO_3$ in Eastman sec-butanol (350 cc) distilling off 170 cc alcohol-water azeotrope, then adding $H_3PO_4$. After further distillation to remove water, the resultant gel was dried and calcined at 260° C. Cupric nitrate hexahydrate (1.60 g) and bismuth nitrate pentahydrate (1.75 g) were dissolved in 2.5 cc of nitric acid and 22.3 cc of water, and added to 25 g $BPO_4$ powder. The paste was dried at 110° C. and heat-treated as in Example 1. The resultant light blue solid had a surface area of 63 m²/g.

EXAMPLE 4

$Fe_{10}Bi_{0.7}P_{12}O_{46}$

Ammonium dihydrogen phosphate (138 g) was dissolved in 100 cc of water with heating. Ferric nitrate nonahydrate (404 g) and bismuth nitrate pentahydrate (35.1 g) were added, in order, to 10 cc of water and heated. The resultant nitrate solution was added to the phosphate solution. A slurry formed which was heated with stirring to remove water, then dried and calcined as in Example 1. The light tan solid obtained had a surface area of 3.8 m²/g.

EXAMPLE 5

$Co_{10}Bi_{0.7}P_{12}O_{41}$

Ammonium dihydrogen phosphate (138 g), cobalt nitrate hexahydrate (291.1 g) and bismuth nitrate pentahydrate (35.1 g) were dissolved and combined as in Example 4. After heat-treatment as in Example 1, by the resulting blue solid had a surface area of 5.4 m²/g.

EXAMPLE 6

$Co_7Fe_3Bi_{0.7}P_{12}O_{43}$

A nitrate solution was made up of cobalt nitrate hexahydrate (203.8 g), ferric nitrate nonahydrate (121.2 g) and bismuth nitrate pentahydrate (35.1 g) with 10 cc of water, and added to an ammonium dihydrogen phosphate (138.0 g) solution as in Example 4. After heat-treatment as in Example 1, the resulting blue solid had a surface of 7.7 m²/g.

EXAMPLE 7

50%$Co_7Fe_3Bi_1P_{12}O_{43}$-50%$BPO_4$

A nitrate solution was made up of cobalt nitrate hexahydrate (85 g), ferric nitrate nonahydrate (50.5 g) and bismuth nitrate pentahydrate (20.2 g) with 5 cc water. It was added to an ammonium dihydrogen phosphate solution (57.5 g) in 100 cc of water to which 53 g boron phosphate prepared as in Example 2, was added. After stirring and heating, the slurry was dried anc calcined as in Example 1. The resulting blue solid had a surface area of 11.9 m²/g.

EXAMPLE 8

$Co_{9.5}Fe_{0.5}BiP_{12}O_{42}$

A nitrate solution was made up of cobalt nitrate hexahydrate (276.5 g), ferric nitrate nonahydrate (20.2 g) and bismuth nitrate pentahydrate (48.5 g). It was added to a solution of ammonium dihydrogen phosphate (138 g) in 100 cc of water, dried and heat-treated as in Example 1. The resulting blue solid had a surface area of 12.6 m²/g.

EXAMPLE 9

$Mg_9FeBiP_{12}O_{42}$

A nitrate solution was made up of magnesium nitrate hexahydrate (115.4 g), ferric nitrate nonahydrate (20.2 g) and bismuth nitrate pentahydrate (24.3 g). It was added to a solution of ammonium dihydrogen phosphate (69 g) in 50 cc water, dried and heat-treated as in Example 1. The resulting cream colored solid had a surface area of 12.0 m²/g.

EXAMPLE 10

$Co_9CrBiP_{12}O_{42}$

A nitrate solution was made up of the cobalt nitrate hexahydrate (131 g), chromium (III) nitrate nonahydrate (20 g), bismuth nitrate pentahydrate (24.3 g) and 5 cc of water. It was added to a solution of ammonium dihydrogen phosphate (69 g) in 50 cc of water, dried and heat-treated as in Example 1. The resulting blue solid had a surface area of 14.3 m²/g.

EXAMPLE 11

$Co_7La_{1.5}Bi_2P_{12}O_{42}$

A nitrate solution was made up of cobalt nitrate hexahydrate (101.9 g), lanthanum nitrate hexahydrate (32.8 g), bismuth nitrate pentahydrate (48.5 g) and 7 cc of concentrated nitric acid. It was added to a solution of ammonium dihydrogen phosphate (69 g) in 50 cc of water, dried and heat-treated as in Example 1, except that 550° C. heat-treated was extended to 16 hours. The resultant blue solid had a surface area of 19.4 m²/g.

EXAMPLE 12

$Co_8La_{0.5}Bi_2P_{12}O_{42}$

A nitrate solution was made up of cobalt nitrate hexahydrate (116.4 g), lanthanum nitrate hexahydrate (10.9 g), bismuth nitrate pentahydrate (48.5 g), and 3 cc of concentrated nitric acid with 10 cc water. It was added to ammonium dihydrogen phosphate (69 g) dissolved in 50 cc water, then dried and heat-treated as in Example 11. The resulting blue solid had a surface area of 7.7 m²/g.

EXAMPLE 13

$Co_9La_{1.0}Bi_1P_{12}O_{42}$

A nitrate solution was made up of cobalt nitrate hexahydrate (131 g), lanthanum nitrate hexahydrate (217. g) and bismuth nitrate pentahydrate (24.3 g) with 10 cc of water. It was added to ammonium dihydrogen phosphate (69 g) dissolved in 50 cc of water. The slurry was dried and heat-treated as in Example 1. The resulting blue solid had a surface area of 10.5 m$^2$/g.

EXAMPLE 14

$K_{0.01}Co_9La_1BiP_{12}O_{42}$

A nitrate solution was prepared as in Example 13. A 10 cc solution of potassium acetate (0.5 g/100 cc) was added to the mixed nitrates, and the nitrate solution was added to an ammonium dihydrogen phosphate solution as in Example 13. The slurry was dried and heat-treated as in Example 11. The resultant blue solid had a surface area of 19.0 m$^2$/g.

EXAMPLE 15

$Co_7Zn_2La_1BiP_{12}O_{42}$

A nitrate solution was made up of cobalt nitrate hexahydrate (101.9 g), zinc nitrate hexahydrate (29.8 g), lanthanum nitrate hexahydrate (21.7 g) and bismuth nitrate pentahydrate (24.3 g) in 5 cc of water. It was added to an ammonium dihydrogen phosphate (69 g) solution in 50 cc of water. After stirring and heating, the slurry was dried and heat-treated as in Example 11. The resultant blue solid had a surface area of 8.6 m$^2$/g.

EXAMPLE 16

$Co_9CeBiP_{13}O_{45}$

Ceric ammonium nitrate (27.4 g) was dissolved in 5 cc nitric acid (concentrated) and 100 cc of water. Bismuth nitrate pentahydrate (24.3 g) and cobalt nitrate hexahydrate (131 g) were added to the ceric solution and dissolved. The resultant solution was added to an ammonium dihydrogen phosphate (74.8 g) solution in 50 cc of water. The resultant slurry was dried and heat-treated as in Example 1. The solid that formed had a surface area of 10.3 m$^2$/g.

EXAMPLE 17

$Mg_9La_1BiP_{12}O_{42}$

A nitrate solution was made up of magnesium nitrate hexahydrate (115.4 g), lanthanum nitrate hexahydrate (21.7 g) and bismuth nitrate pentahydrate (24.3 g) in 10 cc of water. It was added to an ammonium dihydrogen phosphate (69 g) solution in 50 cc of water. After stirring and heating, the slurry was dried and heat-teated as in Example 1. The resultant white solid had a surface area of 27 m$^2$/g.

EXAMPLE 18

$Co_9"Di_1"BiP_{12}O_{42}$

"Didymium" oxide, mixed rare earths (16.5 g) (Trona Corp. Code 422) was dissolved in 25 cc of concentrated nitric acid. Bismuth nitrate pentahydrate (24.3 g) was added to the "didymium" solution which was then added to a solution of ammonium dihydrogen phosphate (69 g) in 50 cc of water. A cobalt nitrate hexahydrate (131 g) solution in 10 cc of water was then added. The slurry was dried and heat-treated as in Example 1. The resultant blue solid had a surface area of 15.4 m$^2$/g.

EXAMPLE 19

$Co_9Fe_1TeP_{12}O_{42.5}$

Tellurium dioxide (8.0 g) was dissolved in 10 cc of nitric acid with warming. This solution was added to a nitrate solution consiting of cobalt nitrate hexahydrate (131 g) and ferric nitrate nonahydrate (20.2 g) and 5 cc of water. The nitrate solution was added to an ammonium dihydrogen phosphate (69 g) solution in 50 cc of water. The slurry was dried at 110° C. and heat-treated as in Example 1, with the final 550° C. stage being performed in the stainless steel reactor. The resultant blue solid had a surface area of 59.9 m$^2$/g.

EXAMPLE 20

$Co_{10}Sb_1 P_{12}O_{41.5}$

A slurry of $Sb_2O_3$ (14.6 g) in 10 cc glacial acetic acid and 10 cc water was added to a solution of ammonium dihydrogen phosphate (69.0 g) in 50 cc of water. A solution of cobalt nitrate hexahydrate (145.5 g) in 10 cc of water was added. After heating and stirring, the slurry was dried and heat-treated as in Example 1.

EXAMPLE 21

$Co_{10}As_1P_{12}O_{41.5}$

A slurry of 9.9 g $As_2O_3$ in 10 cc glacial acetic acid and 40 cc water was added to an ammonium dihydrogen phosphate solution (69.0 g in 50 cc of water). The remainder of the preparation was the same as in Example 20.

EXAMPLE 22

$Co_{10}Cd_2P_{12}O_x$

Cobalt nitrate hexahydrate (145.5 g) and cadmium nitrate tetrahydrate (30.8 g) were dissolved in 10 cc of water. This solution was added to an ammonium dihydrogen phosphate solution (69 g) in 80 cc water. The resultant slurry was dried and heat-treated as in Example 1.

EXAMPLE 23

$Co_8BaFeBiP_{12}O_{42}$

A nitrate solution was made up of cobalt nitrate hexahydrate (116.4 g), bismuth nitrate pentahydrate (24.3 g), ferric nitrate nonahydrate (20.2 g) and 50 cc of water. Barium hydroxide octahydrate (15.8 g) was acidified with 10% solution of concentrated nitric acid in water to a pH of 1.5, then added to the nitrate. The resultant slurry was added to an ammonium dihydrogen phosphate solution (69 g) in 50 cc of water. The slurry was dried and heat-treated as in Example 1, to give a solid with a surface area of 10.6 m$^2$/g.

EXAMPLE 24

$Co_9CeBiP_{12}O_{45}$

The same catalyst as Example 16 was regenerated by passing air over the catalyst at reaction temperature.

EXAMPLE 25

$Mg_9LaBiP_{12}O_{42}$

Same catalyst as Example 17 was regenerated by passing air over the catalyst at reaction temperature.

EXAMPLE 26

$K_{0.1}Co_9Cr_1Bi_1P_{12}O_{42}$

This catalyst was prepared in the same manner as the catalyst of Example 10 except for the addition of potassium acetate (0.49 g) to the nitrate solution. The surface area was 15.2 m²/g.

The number of oxygen atoms in the catalysts in Examples 1 to 26 were estimated. However, the number of oxygens may actually vary from about 30 to 60, depending upon the reaction conditions.

The above catalyst compositions were employed in the oxydehydrogenation of ethyl benzene to styrene, diethyl benzene to divinyl benzene and methyl ethyl pyridine to methyl vinyl pyridine in a fixed-bed reactor comprising a ½-inch O.D. stainless steel tube having a catalyst volume capacity of 15 cc.

A reactant mixture of air, aromatic compound and nitrogen were pre-mixed and fed to the reactor in a molar ratio of 5/1/2, respectively. The reactor was maintained at a temperature of 530°-532° C. and at atmospheric pressure. The liquid hourly space velocity of the aromatic feed over the catalyst was 0.23 hours$^{-1}$, and the contact time was 3.3 seconds. Particle size of the catalyst employed was 20-35 mesh. The percent per pass conversion to the desired alkenyl aromatic compound and the selectivity of the reactions reported in Tables 1 to 3 were calculated in the following manner:

Percent Conversion = $\frac{\text{Moles of alkyl aromatic converted}}{\text{Moles of alkyl aromatic fed}} \times 100$ Percent Single Pass Yield = $\frac{\text{Moles of alkenyl aromatic obtained}}{\text{Moles of alkyl aromatic fed}} \times 100$ Percent Selectivity = $\frac{\text{Moles of alkenyl aromatic obtained}}{\text{Moles of alkyl aromatic converted}} \times 100$

TABLE II
OXYDEHYDROGENATION OF METHYL ETHYL PYRIDINE TO METHYL VINYL PYRIDINE

| Example No. | Catalyst | Mole % Conversion of (Me Et Pyridine) | Mole % Yield of (Me Vinyl Pyridine) | Mole % Selectivity to (Me Vinyl Pyridine) |
|---|---|---|---|---|
| 23 | $Co_8BaFeBiP_{12}O_{42}$ | 35 | 23 | 66 |
| 24 | $Co_9CeBiP_{13}O_{45}$ | 32 | 21 | 66 |
| 25 | $Mg_9LaBiP_{12}O_{42}$ | 40 | 26 | 65 |

TABLE III
OXYDEHYDROGENATION OF DIETHYL BENZENE* TO DIVINYL BENZENE

| Ex. No. | Catalyst | Mole % Conversion of Diethyl Benzene | Mole % Yield of Ethyl-Vinyl & Divinyl Benzene | | Mole % Selectivity to Ethyl Vinyl & Divinyl Benzene |
|---|---|---|---|---|---|
| 26 | $K_{0.1}Co_9Cr_1BiP_{12}O_{42}$ | 78 | 40 | 19 | 76 |

*(Eastman T 1Q31, M, P Mixture)

We claim:
1. The catalyst composition represented by the empirical formula:

$$A_aM_bM^1{}_cM^{11}{}_dB_eP_jO_x$$

wherein
A is an alkali metal and or thallium;
M is one or more elements of nickel, cobalt, copper, manganese, magnesium, zinc, calcium, niobium, tantalum, strontium or barium;

TABLE I
OXYDEHYDROGENATION OF ETHYL BENZENE TO STYRENE

| Example No. | Catalyst | Mole % Conversion of Ethyl Benzene | Mole % Per Pass Yield To Styrene | Mole % Selectivity To Styrene |
|---|---|---|---|---|
| Comp. A | $Ni_2P_2O_7$ | 55 | 43 | 79 |
| Comp. B | $Mg_2P_2O_7$ | 71 | 61 | 86 |
| Comp. C | $La_4(P_2O_7)_3$ | 55 | 41 | 75 |
| Comp. D | $Co_7Fe_3P_{12}O_{41.5}$ | 27 | 24 | 88 |
| Comp. E | $Co_2P_2O_7$ | 47 | 37 | 78 |
| 1 | $Bi_8P_{12}O_{42}$ | 14 | 12.5 | 85 |
| 2 | $25\%Bi_8P_{12}O_{42}$-75%$BPO_4$ | 68 | 59 | 86 |
| 3 | $5\%Cu_{1.5}BiP_5O_{15.5}$-95%$BPO_4$ | 51 | 42 | 82 |
| 4 | $Fe_{10}Bi_{0.7}P_{12}O_{46}$ | 39 | 18 | 72 |
| 5 | $Co_{10}Bi_{0.7}P_{12}O_{41}$ | 55 | 48 | 86 |
| 6 | $Co_7Fe_3Bi_{0.7}P_{12}O_{42.5}$ | 59 | 50 | 85 |
| 7 | $50\%Co_7Fe_3Bi_1P_{12}O_{43}$-50%$BPO_4$ | 62 | 53 | 85 |
| 8 | $Co_{9.5}Fe_{0.5}BiP_{12}O_{42}$ | 75 | 64 | 87 |
| 9 | $Mg_9Fe_1BiP_{12}O_{42}$ | 65 | 55 | 84 |
| 10 | $Co_9CrBiP_{12}O_{42}$ | 74 | 65 | 89 |
| 11 | $Co_7La_{1.5}Bi_2P_{12}O_{42}$ | 75 | 65 | 87 |
| 12 | $Co_8La_{0.5}Bi_2P_{12}O_{42}$ | 69 | 60 | 87 |
| 13 | $Co_9LaBiP_{12}O_{42}$ | 79 | 71 | 90 |
| 14 | $K_{0.01}Co_9La_1BiP_{12}O_{42}$ | 78 | 70 | 90 |
| 15 | $Co_7Zn_2La_1BiP_{12}O_{42}$ | 73 | 66 | 90 |
| 16 | $Co_9CeBiP_{13}O_{45}$ | 77 | 69 | 90 |
| 17 | $Mg_9La_1BiP_{12}O_{42}$ | 78 | 70 | 90 |
| 18 | $Co_9\text{"Di"}_1BiP_{12}O_{42}$ | 63 | 51 | 82 |
| 19 | $Co_9Fe_1TeP_{12}O_{42.5}$ | 60 | 50 | 83 |
| 20 | $Co_{10}Sb_1P_{12}O_{41.5}$ | 58 | 46 | 80 |
| 21 | $Co_{10}As_1P_{12}O_{41.5}$ | 52 | 43 | 83 |
| 22 | $Co_{10}Cd_2P_{12}O_{42}$ | 49 | 42 | 87 |

$M^1$ is one or more of the elements of iron, chromium, uranium, thorium, vanadium, titanium, lanthanum or the other rare earths;

$M^{11}$ is one or more of the elements of tin, boron, lead, germanium, aluminum or tungsten, B is one or more of the elements of bismuth, antimony, and arsenic;

P is phosphorus; and wherein a through y have the following values:

$a = 0$ to 5;
$b = 4$ to 20;
$c = 0.1$ to 10;
$d = 0$ to 4;
$e = 0.1$ to 12;
$y = 8$ to 16;
$x =$ the number of oxygens required to satisfy the valence requirements of the other elements present; and wherein the sum of $2b + 3(c+e)$ is greater than 9 and less than $3y$.

2. The catalyst composition of claim 1 wherein
a is in the range of 0-1;
b is in the range of 4 to 12;
c is in the range of 0.1 to 4;
d is in the range of 0 to 2;
e is in the range of 0.1 to 4; and
the sum of $2b + 3(c+e)$ is greater than 9 and less than $3y$.

3. The catalyst composition of claim 1 wherein M in the catalyst composition is cobalt, $M^1$ is lanthanum, and B is bismuth.

4. The catalyst composition of claim 1 wherein M in the catalyst composition is cobalt, $M^1$ is iron and B is bismuth.

5. The catalyst composition of claim 1 wherein M in the catalyst composition is magnesium, $M^1$ is lanthanum and B is bismuth.

6. The catalyst composition of claim 1 wherein M is selected from the group consisting of magnesium and cobalt.

7. The catalyst composition of claim 1 wherein M' is selected from the group consisting of iron, chromium, uranium, thorium, titanium, lanthanum and rare earth element.

8. The catalyst composition of claim 7 wherein M' is selected from the group consisting of iron and lanthanum.

9. The catalyst composition of claim 1 wherein the catalyst contains tin.

10. The catalyst composition of claim 1 wherein the catalyst contains bismuth and antimony.

11. The catalyst composition of claim 1 wherein the catalyst contains bismuth.

12. The catalyst composition of claim 1 wherein the catalyst contains antimony.

13. The catalyst composition of claim 1 wherein d is 0.

14. The catalyst composition of claim 1 wherein d is greater than 0.

* * * * *